(12) United States Patent
Rubinfeld

(10) Patent No.: US 11,179,031 B1
(45) Date of Patent: *Nov. 23, 2021

(54) VISUAL ACUITY AND COLOR TESTING SYSTEM

(71) Applicant: Eric Rubinfeld, Yonkers, NY (US)

(72) Inventor: Eric Rubinfeld, Yonkers, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/207,589

(22) Filed: Mar. 19, 2021

Related U.S. Application Data

(63) Continuation-in-part of application No. 16/917,091, filed on Jun. 30, 2020, now Pat. No. 10,952,605.

(51) Int. Cl.
*A61B 3/06* (2006.01)
*A61B 3/00* (2006.01)
*G06T 7/50* (2017.01)
*A61B 3/028* (2006.01)

(52) U.S. Cl.
CPC ............ *A61B 3/066* (2013.01); *A61B 3/0041* (2013.01); *G06T 7/50* (2017.01); *A61B 3/028* (2013.01); *A61B 2560/0223* (2013.01); *G06T 2207/10028* (2013.01)

(58) Field of Classification Search
CPC ....... A61B 3/066; A61B 3/0041; A61B 3/028; A61B 2560/0223; G06T 7/50; G06T 2207/10028
USPC ........................................................ 351/242
See application file for complete search history.

(56) References Cited

U.S. PATENT DOCUMENTS 10,952,605 B1 * 3/2021 Rubinfeld ............ A61B 3/0033

* cited by examiner

*Primary Examiner* — Mohammed A Hasan
(74) *Attorney, Agent, or Firm* — RC Trademark Company

(57) ABSTRACT

According to some embodiments, a system and method of testing color vision is disclosed. The system and method of testing color vision comprises initiating a color vision test on a first computing device, linking a program on a second computing device with the color vision test on the first computing device, determining a distance from the first computing device using the second computing device, and transmitting answers to the color vision test using the second computing device wherein the questions associated with the color vision test are displayed on the first computing device.

9 Claims, 4 Drawing Sheets

200 initiating a visual acuity test on a first computing device;
210 linking a program on a second computing device with the visual acuity test on the first computing device
220 determining a distance from the first computing device using the second computing device
230 transmitting answers to the visual acuity test using the second computing device wherein the questions associated with the visual acuity test are displayed on the first computing device.
240

FIG. 2

400 initiating a color vision test on a first computing device;
410

linking a program on a second computing device with the color vision test on the first computing device
420

determining a distance from the first computing device using the second computing device
430

transmitting answers to the color vision test using the second computing device wherein the questions associated with the color vision test are displayed on the first computing device.
440

FIG. 4

VISUAL ACUITY AND COLOR TESTING SYSTEM

BACKGROUND

Pathogens, such as the novel coronavirus (COVID-19) may be spread through aerosols and respiratory droplets that are expelled from a person's mouth or nose when an infected person talks, coughs or sneezes. Because of the rapid spread of COVID-19, people are avoiding crowded areas or areas where people congregate. People who want or need a license to operate a motor vehicle, must be licensed by their state's department of motor vehicles (DMV) which are notorious for long lines and having to wait for long periods of time in a crowded room.

As part of a driving test, or renewal of a driver's license, drivers are required to take a vision test to ensure their vision is adequate for driving. For example, in the state of New York, a driver must pass a vision test when they apply for a driver license or they renew their license. New York's requires that the driver have a visual acuity of at least 20/40 based on the Snellen Visual Acuity Scale with or without corrective lenses. Because these visual acuity tests are given onsite at the DMV or at a local eye doctor, drivers are more susceptible to contracting COVID-19 and therefore, a system to remotely provide a visual acuity test to avoided contracting COVID-19 is desirable.

SUMMARY

Some embodiments described herein relate to a system and method of determining visual acuity. The method comprises initiating a visual acuity test on a first computing device, linking a program or pairing a program embedded in a unique URL on a second computing device with the visual acuity test on the first computing device, determining a distance from the first computing device using the second computing device, and transmitting answers to the visual acuity test using the second computing device wherein the questions associated with the visual acuity test are displayed on the first computing device.

BRIEF DESCRIPTION OF THE DRAWING

FIG. 2 illustrates a method in accordance with some embodiments.

FIG. 4 illustrates a method in accordance with some embodiments.

DETAILED DESCRIPTION

In the following detailed description, numerous specific details are set forth in order to provide a thorough understanding of the embodiments. However, it will be understood by those of ordinary skill in the art that the embodiments may be practiced without these specific details. In other instances, well-known methods, procedures, components and circuits have not been described in detail so as not to obscure the embodiments.

The present embodiments relate to a remote visual acuity testing system that may be conducted away from the DMV or eye doctor's office. In particular, the present embodiments relate to a system that uses (i) a stationary viewing platform such as, for example, a desktop monitor or a laptop and (ii) a portable platform for answering questions displayed on the stationary viewing platform when a user, or driver, is at a predetermined distance from the viewing platform.

Figure 1:
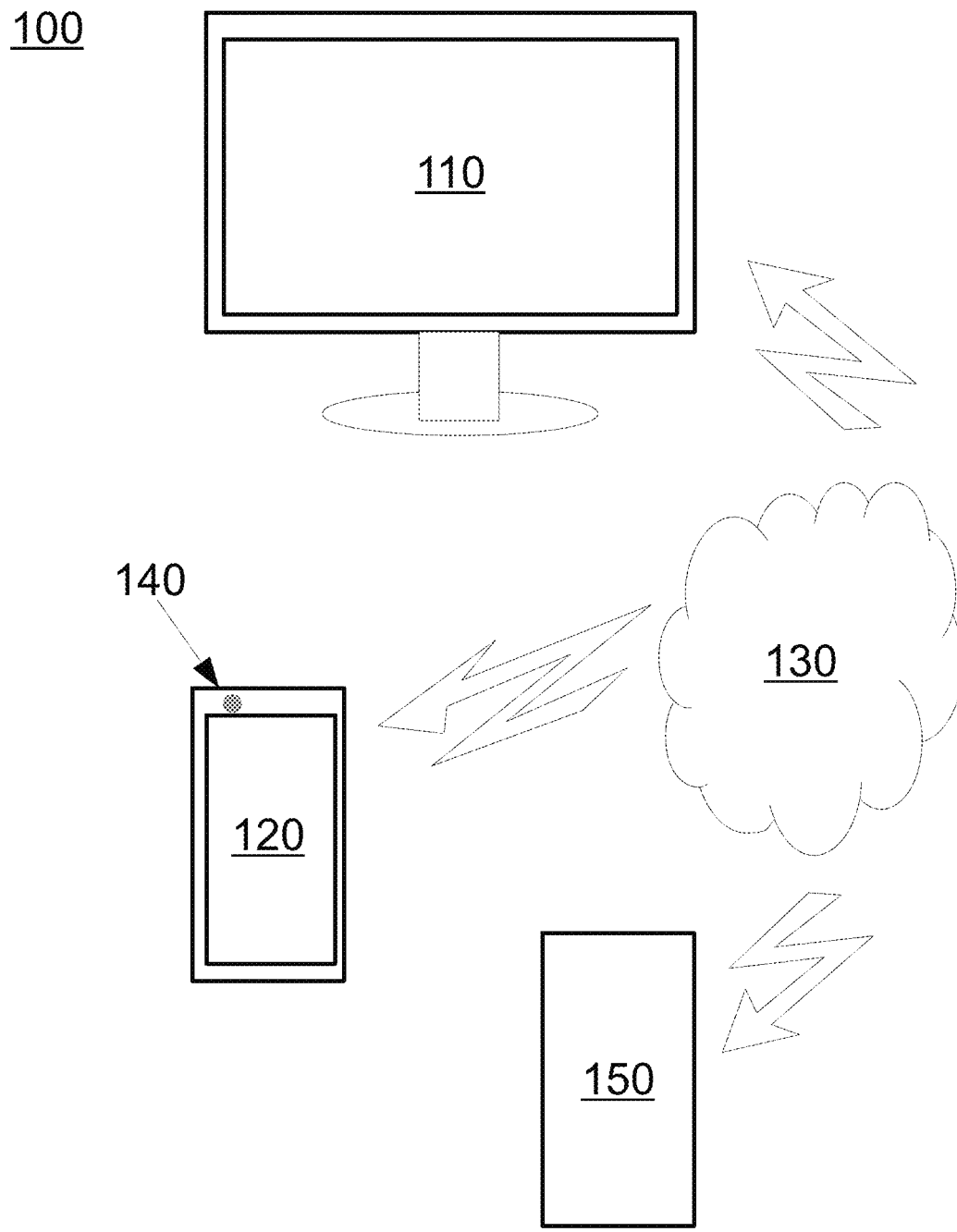
FIG. 1 illustrates a visual acuity system in accordance with some embodiments.

Now referring to FIG. 1, an embodiment of a visual acuity testing system 100 is illustrated. In some embodiments, the visual acuity testing system 100 may also be used as a color vision testing system. As illustrated in FIG. 1, a first computing device 110 and a second computing device 120 may be communicatively coupled to a communication network 130. The communication network 130 may comprise any wired or wireless communication network that may be used for communication purposes between electronic devices. For example, the network 130 may comprise, but is not limited to, a wired and/or wireless mesh network, LAN, MAN, WAN, or the Internet.

For purposes of illustration, the first computing device 110 may comprise a desktop computer, a laptop or a tablet. The first computing device 110 may function as a viewing platform for administering a visual acuity test. The second computing device 120 may comprise a mobile device such as a tablet or a smart phone. In some embodiments, the second computing device 120 may function as a portable platform for answering questions displayed on a stationary viewing platform when a user, or driver, is at a predetermined distance from the first computing device 110. In some embodiments, the second computing device 120 may not allow for a user to answer questions if the user is not at or greater than a predetermined distance away from the first computing device 110. In some embodiments, the first computing device 110 may not start or continue a visual acuity test if the user is not at or greater than a predetermined distance away from the first computing device 110.

To determine distance, the second computing device 120 may include a measuring device 140 such as, but not limited to, a GPS radio, a WIFI radio, a camera and/or an augmented reality laser pointer. The aforementioned measuring devices 140 may be used for determining a distance away from the first computing device 110. In some embodiments, the first computing device 110 and the second computing device 120 may communicate with a back-end or remote server 150 via the communication network 130 as will be explained with respect to FIG. 2.

Now referring to FIG. 2, a method 200 that might be performed by the visual acuity testing system described with respect to FIG. 1 is illustrated according to some embodiments. The method described herein does not imply a fixed order to the steps, and embodiments of the present invention may be practiced in any order that is practicable. Note that any of the methods described herein may be performed by hardware, software, or any combination of these approaches. For example, a non-transitory computer-readable storage medium may store thereon instructions that when executed by a machine result in performance according to any of the embodiments described herein.

Method 200 may relate to administering a visual acuity test while a user or driver is remotely located from the DMV or eye doctors' office such as, but not limited to, at home. One of the main issues of testing visual acuity at home is ensuring that the patient is taking the test at a required distance away from a viewing platform since cheating would be easy if the user stands too close to the viewing platform.

Now referring to 210, a visual acuity test may be initiated on a first computing device. As stated previously, the first computing device may comprise, but is not limited to, a desktop, laptop or tablet computer. The first computing device may be used as a stationary viewing platform and a user may view images on the first computing device from a predetermined distance away from the first computing device.

For purposes of illustrating features of the present embodiments, an example will now be introduced and referenced throughout the disclosure. Those skilled in the art will recognize that this example is illustrative and is not limiting and is provided purely for explanatory purposes. In some embodiments, a driver needs a visual acuity test to renew a driver's license. Instead of having the test performed at their local DMV or eye doctor's office, the driver logs into an online visual acuity system and starts the visual acuity test. The test may be hosted by a remote server that is in communication with the first computing device. The test may start by first linking a program on a second computing device or pairing a program embedded in a unique URL with the visual acuity test on the first computing device at 220.

Linking the second computing device, to work in conjunction with the first computing device, may comprise entering a phone number of the second computing device (e.g., a mobile device) so that a text message may be sent to the second computing device from the remote sever with a link such as a unique URL for an individual user being tested. In this case, the user can login to the visual acuity system using the link provided in the text message. In some embodiments, login identification may be displayed on the first computing device so that a user may enter the login information into a web browser on the second computing device to synchronize the second computing device with the first computing device. In some embodiments, the first computing device and the second computing devices will each use a browser to either conduct the test and to answer questions. In this embodiment, the second computing device may use a different authentication URL than the first computing device. This authentication URL may link the second computing device to the first computing device for purposes of conducting the visual acuity test.

Since the first computing device may comprise a variety of screen sizes (e.g., ranging from 10" diagonal to 32" diagonal), a display on a screen associated with the first computing device may be calibrated prior to starting the visual acuity test. Calibration may comprise adjusting a shape on the screen associated with the first computing device to match a size of a corresponding reference shape. For example, a user may use a physical object such as a 4"×6" rectangle or another shaped object. In some embodiments, a user may enter his cell phone make and model into a setup screen and a known size of that phone may be used to create an image on the screen. For example, an iPhone 12 screen size is 5.4 inches. If a user enters an iPhone 12, a rectangle with a 5.4-inch diagonal size may be displayed on the screen. A slider, or other type of adjustment control, may be used to change the size of the rectangle on the screen so that it matches the users 5.4-inch iPhone 12 screen. Once the size of the screen matches the selected phone or another physical object, the user may select a calibration button to indicate that the display on the first computing device has been calibrated.

In some embodiments, this calibration may be automated based on the camera in the phone that can measure a size of the display object and report back to the remote server which then sends instructions to the first computing device to make adjustments on the first computing device. For example, if a displayed object on a screen of the first computing device measures 4 inches diagonally based on the iPhone 12's measurement, the iPhone 12 may report to the remote server that the size has to be increased by 1.4 inches. The remote server may then send a message to the first computing device to automatically adjust the screen size.

Next, at 230, a distance that the user is located from the first computing device may be determined using the second computing device. In some embodiments, the second computing device comprises a camera and determining a distance that the user is located from the first computing device may be based on the second computing device being pointed to a computer monitor frame associated with the first computing device. As a user walks away from the computer monitor frame, the second computing may indicate by either visual indicator or an auditory sound that the user has reached a predetermined distance from the first computing device. This indication may be based on entering a size of the computer monitor frame of the first computing device (e.g., 21") or having the mobile device automatically determine a size of the computer monitor frame. As a user walks away from the computer monitor frame, the second computing device may determine, based on viewing the computer monitor frame, a distance that a user should be from the computer monitor frame. Thus the camera and an onboard processor may calculate a determined distance away from the computer monitor frame based on a known size of the computer monitor frame and this information may be transmitted to the first computing device which may use this information to determine when the user is at a proper distance to take the test.

In some embodiments, the second computing device comprises an augmented reality laser pointer that is pointed to the computer monitor frame of the first computing device. In some embodiments, a camera in the second computing device may be used for determining a distance using augmented reality. As a user walks away from the computer monitor frame, the second augmented reality laser pointer, or camera, may indicate by either visual indicator or an auditory sound that the user has reached a predetermined distance from the first computing device. This indication may be based on the augmented reality laser pointer, or camera, determining a time it takes the laser to reach a display screen associated with the first computing device. As a user walks away from the display screen, the second computing device may determine, based on the augmented reality laser pointer, or camera, a distance that a user should be from the computer monitor frame and the first computing device may use this information to determine when the user is at a proper distance to take the test. In some embodiments, a circular augmented reality fence may be utilized. A radius of the fence may be at a predetermined distance from the first computing device. For example, the radius may be 10 feet and thus the visual acuity test may function as long as the user is within a 10 foot from the first computing device (or a display screen associated with the first computing device). The augmented reality measuring may be embedded in the unique URL for the second device. This URL may be unique to each person taking the visual acuity test. In some embodiments, the display screen may display Snellen letter(s) and a size of the letters may be based on the user's state's requirements. In this case, when the user registers to take the visual acuity test, the required parameters regarding the size of the letters may be determined to provide a correct visual acuity test. As a user aims the augmented reality laser pointer, or camera, at the display screen associated with the first computing device, the second computing device may display a first color (e.g., red) until the user reaches a correct distance (e.g., 10 ft) and, in this case, the screen associated with the second computing device may change to a second color (e.g., green). This change in color may indicate to a user that they are at a proper distance and can take the visual acuity test. Also, in some embodiments, when the change in color occurs, a message may be sent to the first computing that indicates that a user is at the defined distance.

In some embodiments, the second computing device marks a location of the first computing device when the second computing device is within close proximity to the first computing device. This may be performed by capturing one or more coordinates associated with the first computing device. The coordinates may be, for example, GPS coordinates so the GPS location of the first computing device is known. This marking may also capturing a signal strength of a WIFI router to determine a distance from the router. The user may then move away from the first computing device and be notified by either visual indicator or an auditory sound that the user has reached a predetermined distance from the first computing device based on new coordinates determined by the second computing device and/or a signal strength of the WIFI router.

For example, distance may be based on a combination of using round-trip time (RTT) such as Wi-Fi RTT, GPS dual-frequency and carrier phase measurements. Wi-Fi RTT ranging and indoor position estimation may be based on making measurements of the time of flight of RF signals, and may be used to accurately estimate an indoor position of the user.

Once a user is at a predetermined distance from the first computing device, at 240, answers to the visual acuity test may be transmitted using the second computing device wherein the questions associated with the visual acuity test are displayed on the first computing device. Answers submitted on the second computing device may be transmitted to the remote server where the test is scored. In some embodiments, the answers may be scored by the first computing device. The user may be notified of its test score or the test score may be stored and transmitted to a third party (e.g., the DMV or eye doctor's office).

Figure 3:
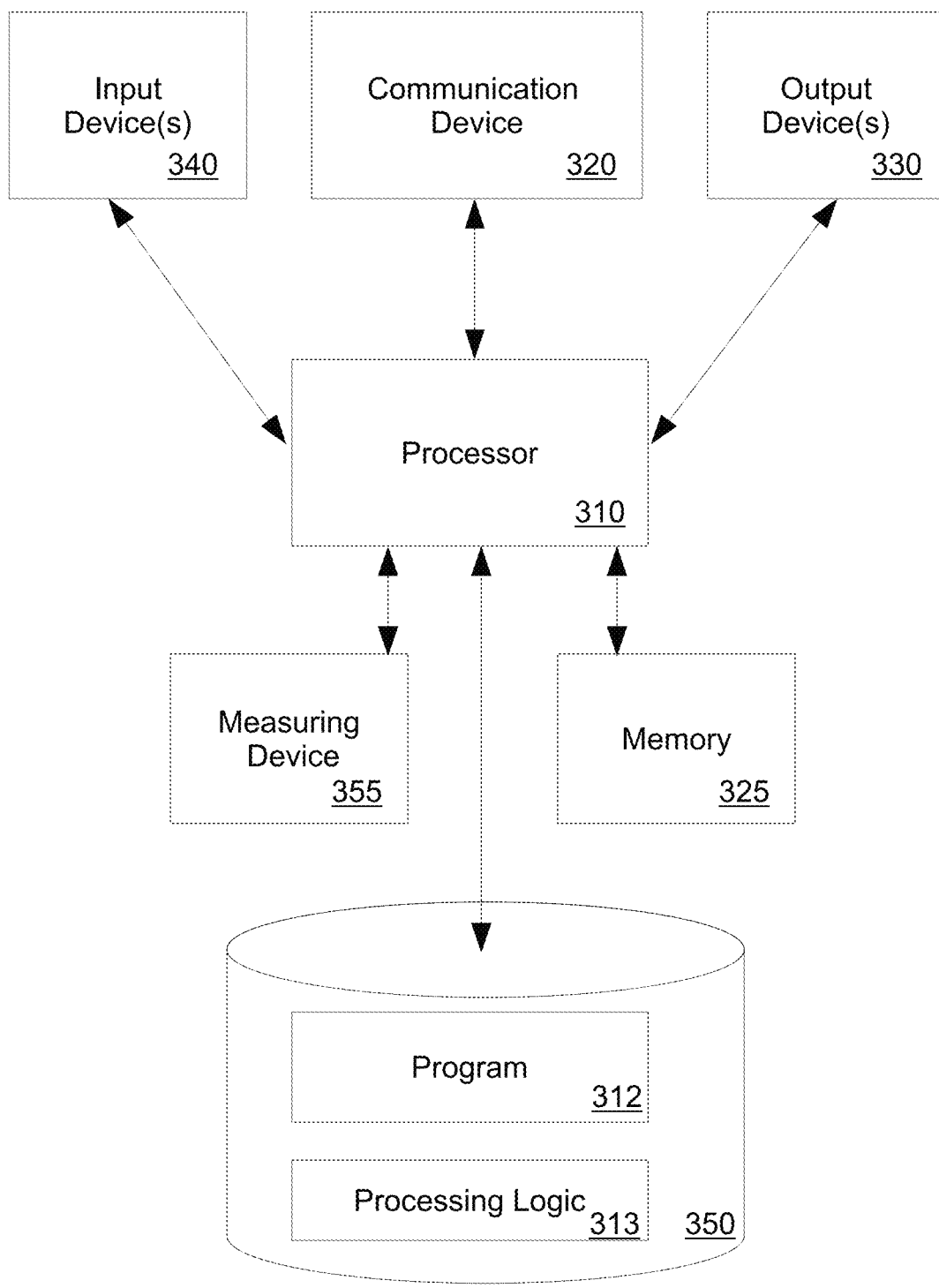
FIG. 3 illustrates a remote device in accordance with some embodiments.

Note the embodiments described herein may be implemented using any number of different hardware configurations. For example, FIG. 3 illustrates a mobile device 300 that may be, for example, associated with the visual acuity system 100 of FIG. 1. The mobile device 300 may provide a technical and commercial advantage by being able to determine a distance a user is away from a display screen so that a safe visual acuity test may be performed at home.

The mobile device 300 may comprise a processor 310 ("processor"), such as one or more commercially available Central Processing Units (CPUs) in the form of one-chip microprocessors, coupled to a communication device 320 configured to communicate via a communication network (not shown in FIG. 3). The communication device 320 may be used to communicate, for example, with one or more machines on a network. The mobile device 300 further includes an input device 340 (e.g., a mouse and/or keyboard to enter answers to a visual acuity test) and an output device 330 (e.g., to output and display the data and/or alerts). The mobile device 300 may further comprise a measuring device 355. The measuring device 355 may comprise a GPS radio, a camera, a radio transceiver and/or an augmented reality laser pointer.

The processor 310 also communicates with a memory 325 and storage device 350 that stores data 313. The storage device 350 may comprise any appropriate information storage device, including combinations of magnetic storage devices (e.g., a hard disk drive), optical storage devices, mobile telephones, and/or semiconductor memory devices.

The storage device 350 may store a program 312 and/or processing logic 313 for controlling the processor 310. The processor 310 performs instructions of the programs 312, 313, and thereby operates in accordance with any of the embodiments described herein. For example, the processor 310 may receive distance data may institute an alert to a user via the instructions of the programs 312 and processing logic 313.

The programs 312, 313 may be stored in a compiled, compressed, uncompiled and/or encrypted format or a combination. The programs 312, 313 may furthermore include other program elements, such as an operating system, a database management system, and/or device drivers used by the processor 310 to interface with peripheral devices.

In some embodiments, a color vision testing system may be implemented in a similar fashion to the visual acuity system and method described above. For example, the color vision testing may use the same pairing method that is used for the visual acuity test and patients may also use a mobile device to enter in answers or respond to questions. The color vision test implemented by the above system may comprise any conventional color vision test that is required be performed at a specific distance between a patient and a screen.

Now referring to FIG. 4, a method 400 that might be performed by the system described with respect to FIG. 1 is illustrated according to some embodiments. The method described herein does not imply a fixed order to the steps, and embodiments of the present invention may be practiced in any order that is practicable. Note that any of the methods described herein may be performed by hardware, software, or any combination of these approaches. For example, a non-transitory computer-readable storage medium may store thereon instructions that when executed by a machine result in performance according to any of the embodiments described herein.

Method 400 may relate to administering a color vision test while a user is remotely located from the DMV or eye doctors' office such as, but not limited to, at home.

Now referring to 410, a color vision test may be initiated on a first computing device. As stated previously, the first computing device may comprise, but is not limited to, a desktop, laptop or tablet computer. The first computing device may be used as a stationary viewing platform and a user may view images on the first computing device from a predetermined distance away from the first computing device.

The test may start by first linking a program on a second computing device or pairing a program embedded in a unique URL with the color vision test on the first computing device at 420.

Linking the second computing device, to work in conjunction with the first computing device, may comprise entering a phone number of the second computing device (e.g., a mobile device) so that a text message may be sent to the second computing device from the remote sever with a link such as a unique URI, for an individual user being tested. In this case, the user can login to the system using the link provided in the text message. In some embodiments, login identification may be displayed on the first computing device so that a user may enter the login information into a web browser on the second computing device to synchronize the second computing device with the first computing device. In some embodiments, the first computing device and the second computing devices will each use a browser to either conduct the test and to answer questions. In this embodiment, the second computing device may use a different authentication URL than the first computing device.

This authentication URL may link the second computing device to the first computing device for purposes of conducting the color vision test.

Since the first computing device may comprise a variety of screen sizes (e.g., ranging from 10" diagonal to 32" diagonal), a display on a screen associated with the first computing device may be calibrated prior to starting the color vision test. Calibration may comprise adjusting a shape on the screen associated with the first computing device to match a size of a corresponding reference shape. For example, a user may use a physical object such as a 4"×6" rectangle or another shaped object. In some embodiments, a user may enter his cell phone make and model into a setup screen and a known size of that phone may be used to create an image on the screen. For example, an iPhone 12 screen size is 5.4 inches. If a user enters an iPhone 12, a rectangle with a 5.4-inch diagonal size may be displayed on the screen. A slider, or other type of adjustment control, may be used to change the size of the rectangle on the screen so that it matches the users 5.4-inch iPhone 12 screen. Once the size of the screen matches the selected phone or another physical object, the user may select a calibration button to indicate that the display on the first computing device has been calibrated.

In some embodiments, this calibration may be automated based on the camera in the phone that can measure a size of the display object and report back to the remote server which then sends instructions to the first computing device to make adjustments on the first computing device. For example, if a displayed object on a screen of the first computing device measures 4 inches diagonally based on the iPhone 12's measurement, the iPhone 12 may report to the remote server that the size has to be increased by 1.4 inches. The remote server may then send a message to the first computing device to automatically adjust the screen size.

Next, at 430, a distance that the user is located from the first computing device may be determined using the second computing device. In some embodiments, the second computing device comprises a camera and determining a distance that the user is located from the first computing device may be based on the second computing device being pointed to a computer monitor frame associated with the first computing device. As a user walks away from the computer monitor frame, the second computing may indicate by either visual indicator or an auditory sound that the user has reached a predetermined distance from the first computing device. This indication may be based on entering a size of the computer monitor frame of the first computing device (e.g., 21") or having the mobile device automatically determine a size of the computer monitor frame. As a user walks away from the computer monitor frame, the second computing device may determine, based on viewing the computer monitor frame, a distance that a user should be from the computer monitor frame. Thus, the camera and an onboard processor may calculate a determined distance away from the computer monitor frame based on a known size of the computer monitor frame and this information may be transmitted to the first computing device which may use this information to determine when the user is at a proper distance to take the test.

In some embodiments, the second computing device comprises an augmented reality laser pointer that is pointed to the computer monitor frame of the first computing device. In some embodiments, a camera in the second computing device may be used for determining a distance using augmented reality. As a user walks away from the computer monitor frame, the second augmented reality laser pointer, or camera, may indicate by either visual indicator or an auditory sound that the user has reached a predetermined distance from the first computing device. This indication may be based on the augmented reality laser pointer, or camera, determining a time it takes the laser to reach a display screen associated with the first computing device. As a user walks away from the display screen, the second computing device may determine, based on the augmented reality laser pointer, or camera, a distance that a user should be from the computer monitor frame and the first computing device may use this information to determine when the user is at a proper distance to take the test. In some embodiments, a circular augmented reality fence may be utilized. A radius of the fence may be at a predetermined distance from the first computing device. For example, the radius may be 10 feet and thus the color vision test may function as long as the user is within a 10 foot from the first computing device (or a display screen associated with the first computing device). The augmented reality measuring may be embedded in the unique URL, for the second device. This URL may be unique to each person taking the color vision test. In some embodiments, the display screen may display Snellen letter(s) and a size of the letters may be based on the user's state's requirements. In this case, when the user registers to take the color vision test, the required parameters regarding the size of the letters may be determined to provide a correct color vision test. As a user aims the augmented reality laser pointer, or camera, at the display screen associated with the first computing device, the second computing device may display a first color (e.g., red) until the user reaches a correct distance (e.g., 10 ft) and, in this case, the screen associated with the second computing device may, change to a second color (e.g., green). This change in color may indicate to a user that they are at a proper distance and can take the color vision test. Also, in some embodiments, when the change in color occurs, a message may be sent to the first computing that indicates that a user is at the defined distance.

In some embodiments, the second computing device marks a location of the first computing device when the second computing device is within close proximity to the first computing device. This may be performed by capturing one or more coordinates associated with the first computing device. The coordinates may be, for example, GPS coordinates so the GPS location of the first computing device is known. This marking may also capture a signal strength of a WIFI router to determine a distance from the router. The user may then move away from the first computing device and be notified by either visual indicator or an auditory sound that the user has reached a predetermined distance from the first computing device based on new coordinates determined by the second computing device and/or a signal strength of the WIFI router.

For example, distance may be based on a combination of using round-trip time (RTT) such as RTT, GPS dual-frequency and carrier phase measurements. Wi-Fi RTT ranging and indoor position estimation may be based on making measurements of the time of flight of RF signals, and may be used to accurately estimate an indoor position of the user.

Once a user is at a predetermined distance from the first computing device, at 440, answers to the color vision test may be transmitted using the second computing device wherein the questions associated with the color vision test are displayed on the first computing device. Answers submitted on the second computing device may be transmitted to the remote server where the test is scored. In some embodiments, the answers may be scored by the first computing device. The user may be notified of its test score or the test score may be stored and transmitted to a third party (e.g., the DMV or eye doctor's office).

As will be appreciated by one skilled in the art, the present embodiments may be embodied as a system, method or computer program product. Accordingly, the embodiments described herein may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the embodiments described herein may take the form of a computer program product embodied in one or more computer readable medium(s) having computer readable program code embodied thereon.

The process flow and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein. The method steps can then be carried out using the distinct software modules and/or sub-modules of the system, as described above, executing on one or more hardware processors. Further, a computer program product can include a computer-readable storage medium with code adapted to be implemented to carry out one or more method steps described herein, including the provision of the system with the distinct software modules.

This written description uses examples to disclose multiple embodiments, including the preferred embodiments, and also to enable any person skilled in the art to practice the invention, including making and using any devices or systems and performing any incorporated methods. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

What is claimed:

1. A color vision testing system, the system comprising:
   a first computing device to display a color vision test, the first computing device calibrated for the color vision test by adjusting a shape on a screen associated with the first computing device to match a size of a corresponding reference shape; and
   a second computing device to determine a distance from the first computing device and to answer questions associated with the color vision test, wherein the second computing device marks a location of the first computing device when the second computing device is within close proximity to the first computing device by capturing one or more coordinates associated with the first computing device and wherein the second computing indicates by either visual indicator or an auditory sound that a user has reached a predetermined distance from the first computing device based on coordinates determined by the second computing device.

2. The color vision testing system of claim 1, wherein the second computing device comprises a camera.

3. The color vision testing system of claim 1, wherein the second computing device comprises an augmented reality laser pointer.

4. A method of testing color vision, the method comprising:
   initiating a color vision test on a first computing device;
   calibrating the color vision test on the first computing device by adjusting a shape on a screen associated with the first computing device to match a size of a corresponding reference shape;
   linking a program on a second computing device with the color vision test on the first computing device; and
   determining a distance from the first computing device using the second computing device by (i) marking a location of the first computing device using the second computing device when the second computing is within close proximity to the first computing device by capturing one or more coordinates of the first computing device, and (ii) indicating by either visual indicator or an auditory sound that a user has reached a predetermined distance from the first computing device based on coordinates determined by the second computing device;
   transmitting answers to the color vision test using the second computing device wherein the questions associated with the color vision test are displayed on the first computing device.

5. The method of claim 4, wherein the second computing device comprises a camera.

6. The method of claim 4, wherein the second computing device comprises an augmented reality laser.

7. A non-transitory computer-readable medium comprising processor steps that when executed by a processor perform a method of testing color vision, the method comprising:
   initiating a color vision test on a first computing device;
   calibrating the color vision test by adjusting a shape on a screen associated with the first computing device to match a size of a corresponding reference shape;
   linking a program on a second computing device with the color vision test on the first computing device; and
   determining a distance from the first computing device using the second computing device by (i) marking a location of the first computing device using the second computing device when the second computing is within close proximity to the first computing device by capturing one or more coordinates of the first computing device, and (ii) indicating by either visual indicator or an auditory sound that a user has reached a predetermined distance from the first computing device based on coordinates determined by the second computing device;

transmitting answers to the color vision test using the second computing device wherein the questions associated with the color vision test are displayed on the first computing device.

8. The medium of claim 7, wherein the second computing device comprises a camera.

9. The medium of claim 7, wherein the second computing device comprises an augmented reality laser pointer.

* * * * *